(12) United States Patent
Osadchy et al.

(10) Patent No.: US 10,856,768 B2
(45) Date of Patent: Dec. 8, 2020

(54) INTRA-CARDIAC SCAR TISSUE IDENTIFICATION USING IMPEDANCE SENSING AND CONTACT MEASUREMENT

(71) Applicant: BIOSENSE WEBSTER (ISRAEL) LTD., Yokneam (IL)

(72) Inventors: Daniel Osadchy, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 151 days.

(21) Appl. No.: 15/879,630

(22) Filed: Jan. 25, 2018

(65) Prior Publication Data

US 2019/0223753 A1 Jul. 25, 2019

(51) Int. Cl.
| | | |
|---|---|---|
| A61B 5/05 | (2006.01) | |
| A61B 5/00 | (2006.01) | |
| A61B 18/14 | (2006.01) | |
| A61B 5/0464 | (2006.01) | |
| A61B 18/00 | (2006.01) | |
| A61N 1/05 | (2006.01) | |

(52) U.S. Cl.
CPC .......... *A61B 5/0538* (2013.01); *A61B 5/6843* (2013.01); *A61B 5/6847* (2013.01); *A61B 18/1492* (2013.01); *A61B 5/0464* (2013.01); *A61B 5/0537* (2013.01); *A61B 2018/0016* (2013.01); *A61B 2018/00351* (2013.01); *A61B 2018/00875* (2013.01); *A61N 1/05* (2013.01)

(58) Field of Classification Search
USPC .............................................. 600/508–509
See application file for complete search history.

(56) References Cited

U.S. PATENT DOCUMENTS

| | | |
|---|---|---|
| 5,673,704 A | 10/1997 | Marchlinski et al. |
| 2013/0023784 A1 | 1/2013 | Schneider et al. |
| 2013/0072774 A1 | 3/2013 | Greenspan |
| 2014/0155722 A1 | 6/2014 | Greenspan et al. |
| 2015/0032171 A1 | 1/2015 | Ghosh |
| 2016/0183824 A1* | 6/2016 | Severino .............. A61B 5/0432 600/523 |
| 2016/0235303 A1* | 8/2016 | Fleming ............... A61B 5/0066 |

FOREIGN PATENT DOCUMENTS

WO WO 2016/181318 11/2016

OTHER PUBLICATIONS

Pending U.S. Appl. No. 15/610,865, filed Jun. 1, 2017.
Pending U.S. Appl. No. 15/788,286, filed Oct. 19, 2017.
European Search Report dated May 15, 2019 from corresponding European Patent Application No. 19153429.6.

* cited by examiner

*Primary Examiner* — Nicole F Lavert

(57) ABSTRACT

A system includes an electrical interface and a processor. The electrical interface is configured for communicating with a probe inserted into a heart of a patient. The processor is configured to receive, via the electrical interface, (i) a first indication of an electrical impedance measured by the probe at a given location on an inner surface of the heart, and (ii) a second indication of a quality of mechanical contact between the probe and the inner surface of the heart during measurement of the electrical impedance. The processor is further configured, based on the first and second indications, to classify tissue at the given location as scar tissue.

20 Claims, 2 Drawing Sheets

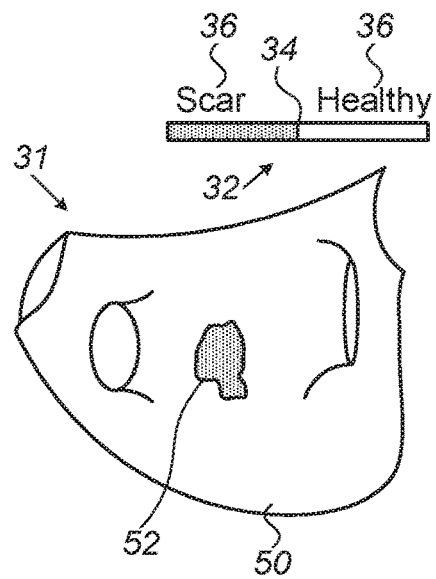
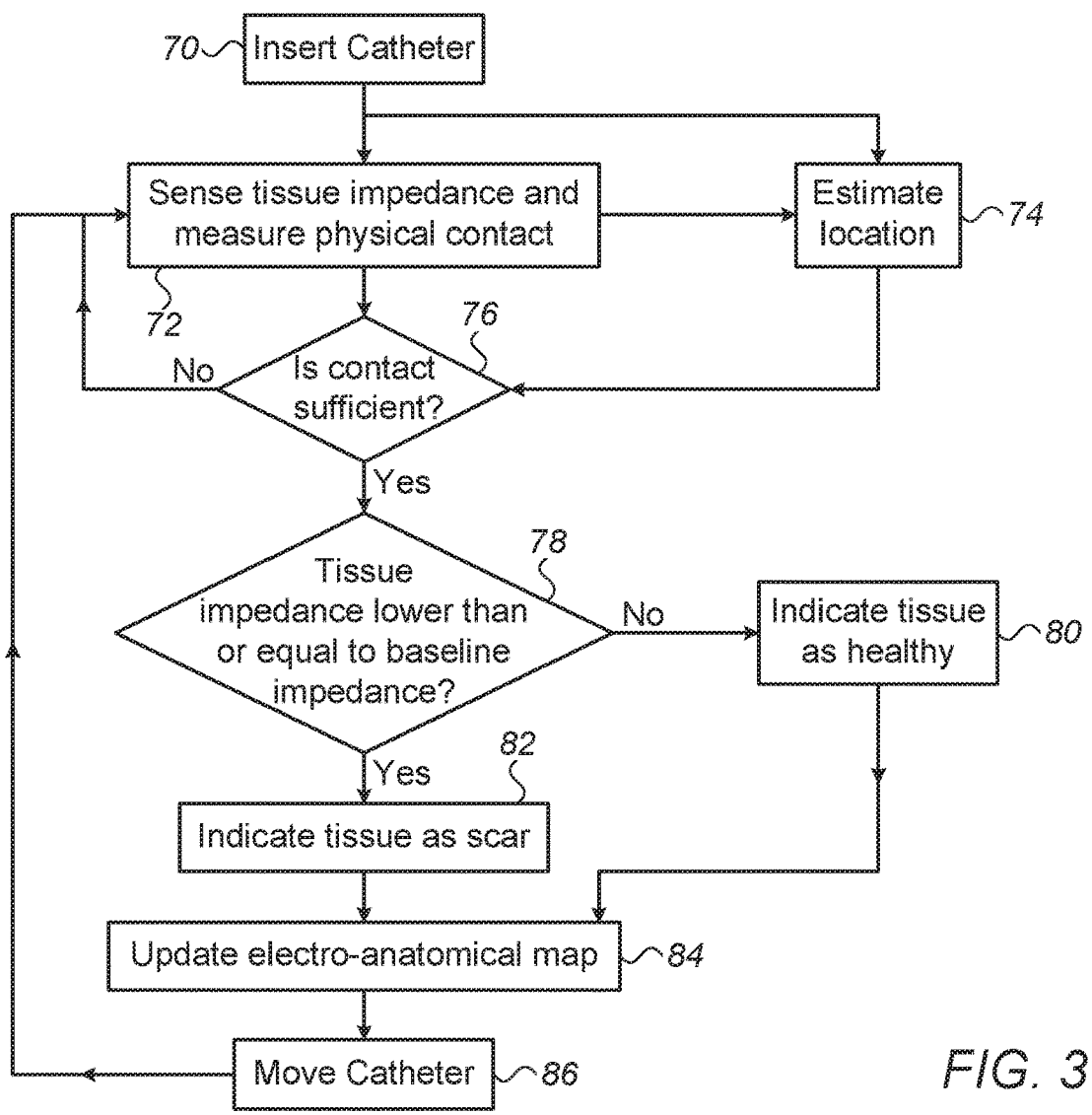
FIG. 2
FIG. 3

INTRA-CARDIAC SCAR TISSUE IDENTIFICATION USING IMPEDANCE SENSING AND CONTACT MEASUREMENT

FIELD OF THE INVENTION

The present invention relates generally to cardiac mapping, and particularly to mapping of intra-cardiac scar tissue.

BACKGROUND OF THE INVENTION

Invasive cardiac procedures often employ techniques for mapping electro-anatomical properties of cardiac tissue. For example, U.S. Patent Application Publication 2013/0072774 describes a method and system for determining the mechanism of cardiac arrhythmia in a patient. The method basically entails measuring the impedance of cardiac tissue in a portion of the patient's heart using a catheter so as to produce an iso-impedance map of that cardiac tissue on a video display and analyzing the pattern of the iso-impedance map to differentiate focal arrhythmia caused by a circumscribed region of focal firing. The method can also be used to identify regions of coherent rapidly conducting tissue, to identify focal "mother rotors" throughout the left atrium that may participate in the generation and maintenance of atrial fibrillation.

As another example, U.S. Pat. No. 5,673,704 describes a method of locating infarcted myocardial tissue in a beating heart. The method includes inserting an impedance measuring tip of a catheter into the chamber of the beating heart, particularly the left or right ventricle, and measuring the impedance of the endocardium at various locations within the chamber of the beating heart. The values measured are compared to impedance values with a predetermined range of values to identify an infarcted area of myocardium and distinguish such area from normal myocardium. The measurements are also compared to a range of values for an infarction border zone. In accordance with the invention, the infarction border zone may be located. The infarction border zone is a significant source of arrhythmia, and particularly of ventricular tachycardia. Further, in accordance with the methods of the present invention, the risk of arrhythmia in a beating heart may be substantially reduced or eliminated by ablating endocardium within the infarction border zone utilizing the same catheter tip. Impedance measurements may also be utilized to assess the adequacy of the electrode-tissue contact, particularly in a fluid filled body organ or cavity.

SUMMARY OF THE INVENTION

An embodiment of the present invention provides a system including an electrical interface and a processor. The electrical interface is configured for communicating with a probe inserted into a heart of a patient. The processor is configured to receive, via the electrical interface, (i) a first indication of an electrical impedance measured by the probe at a given location on an inner surface of the heart, and (ii) a second indication of a quality of mechanical contact between the probe and the inner surface of the heart during measurement of the electrical impedance. The processor is further configured, based on the first and second indications, to classify tissue at the given location as scar tissue.

In some embodiments, the processor is configured to distinguish, based on the second indication, between the scar tissue and blood. In some embodiments, the processor is configured to classify the tissue as the scar tissue by detecting that the tissue has an impedance lower than a given baseline impedance. In an embodiment, the baseline impedance includes a measured blood impedance in the heart. In another embodiment, the baseline impedance includes a measured tissue impedance averaged over a portion of the inner surface of the heart.

In some embodiments, the processor is configured to receive the second indication from one or more sensors that are fitted at a distal end of the probe. In some embodiments, the processor is configured to calculate from the first indication a respective estimated location of the probe in the heart. In an embodiment, the processor is configured to update a map of at least part of the heart by incorporating the estimated location of the probe into the map.

In another embodiment, the processor is configured to update the map with the measured electrical impedance at the estimated location. In some embodiments, the processor is configured to differentiate the scar tissue from healthy tissue on the map using at least one of numerical and visual coding.

There is additionally provided, in accordance with an embodiment of the present invention, a method for detecting intra-cardiac scar tissue. The method includes receiving, from a probe inserted into a heart of a patient, (i) a first indication of an electrical impedance measured by the probe at a given location on an inner surface of the heart, and (ii) a second indication of a quality of mechanical contact between the probe and the inner surface of the heart during measurement of the electrical impedance. Based on the first and second indications, tissue at the given location is classified as scar tissue.

The present invention will be more fully understood from the following detailed description of the embodiments thereof, taken together with the drawings in which:

BRIEF DESCRIPTION OF THE DRAWINGS

FIG. 2 is a schematic, pictorial illustration of an electro-anatomical map of a portion of a patient's heart, in accordance with an embodiment of the present invention; and FIG. 3 is a flow chart that schematically illustrates a method for identifying intra-cardiac scars, in accordance with an embodiment of the present invention.

DETAILED DESCRIPTION OF EMBODIMENTS

Overview

Figure 1:
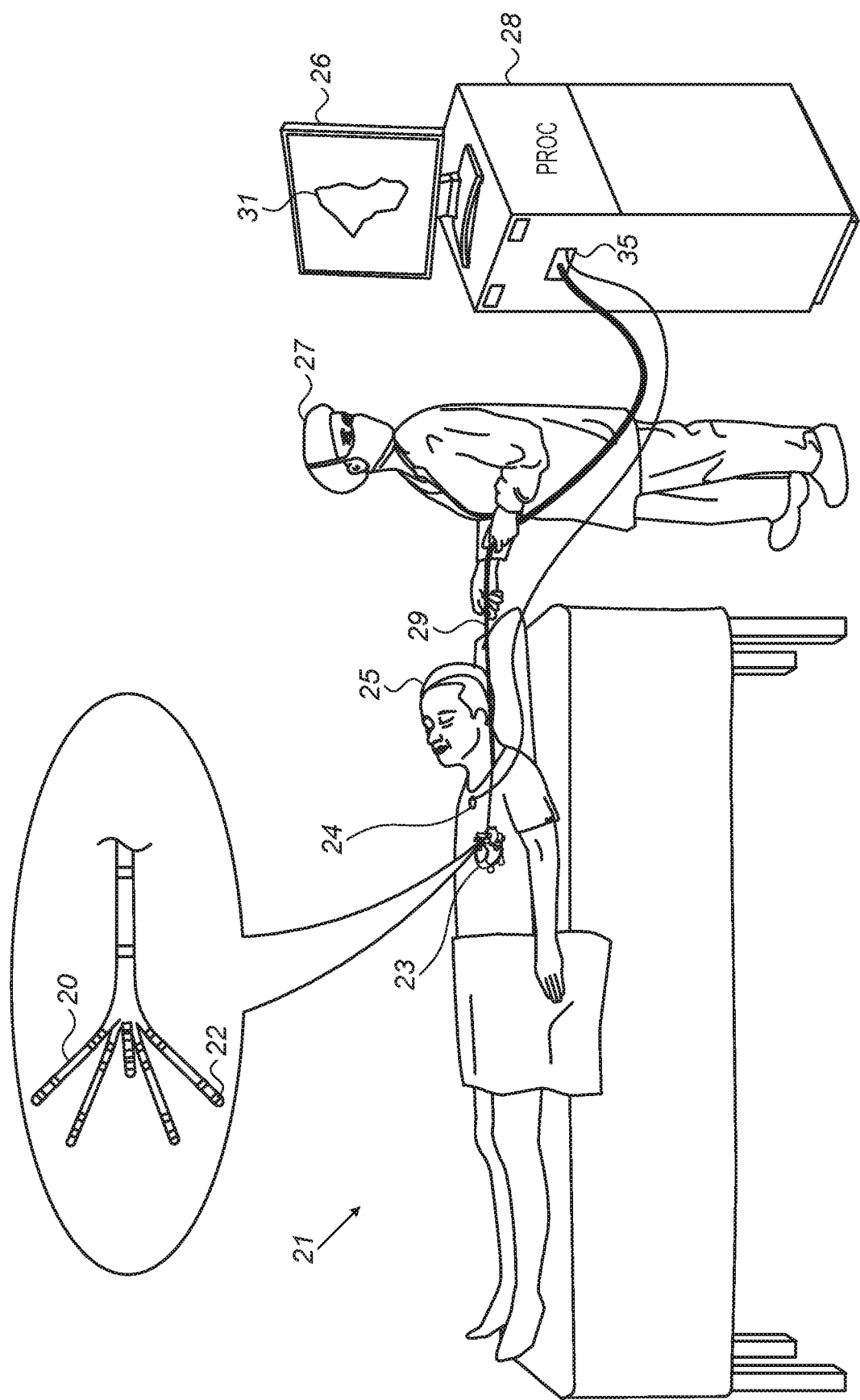
FIG. 1 is a schematic, pictorial illustration of a system for electro-anatomical mapping, in accordance with an embodiment of the present invention.

Embodiments of the present invention that are described herein provide systems and methods for identification of intra-cardiac scar tissue. In some embodiments, a map indicating scar and healthy tissue of an inner wall of a heart is created. The map may be used for any diagnostic/therapeutic procedure that can benefit from identifying scar tissue, such as selecting an appropriate ablation site, and ruling out locations that were already ablated.

In some embodiments, an electro-anatomical mapping system is provided, which uses an electro-anatomical mapping catheter having electrical-potential sensing electrodes fitted at its distal end. The electro-anatomical mapping catheter is used for obtaining tissue impedance measurements of selected points on an inner wall tissue of a heart.

The measured electrical impedance of healthy heart tissue is typically higher than the measured blood impedance, which is seen as an increased measured electrode impedance at and/or nearby a healthy tissue. The measured impedance of a scar, on the other hand, is typically similar or lower than that of blood, which is seen as a lowered measured electrode impedance. Thus, scar tissue may be identified as an area in which the electrical impedance is particularly low.

A challenge, when attempting to differentiate an intra-cardiac scar tissue from healthy tissue and/or blood, is that it is difficult to distinguish between scar tissue and blood using impedance measurements alone. For example, a low impedance reading may result from measuring scar tissue, or from measuring any tissue without making good mechanical contact between the tissue and the electrical-sensing electrodes. Consequently, for example, it may be unclear whether or how the location of a given electrode, and/or any information carried by an impedance signal received from the electrode, should be incorporated into a map, such as an electro-anatomical map, under construction.

To address this challenge, in some embodiments the disclosed system ascertaining sufficient mechanical contact of the electrodes with the tissue, in parallel with measuring tissue impedance, so as to make the distinction between blood and scar tissue possible. In some embodiments, the mechanical contact with the tissue is ascertained by tracking the shape of the catheter's flexible distal end as it changes when it comes in contact with tissue. In other embodiments, sufficient contact with tissue is ascertained by one or more sensors, which are fitted at the distal end of the electro-anatomical mapping catheter and provide a measure of the contact. Such sensors may comprise, for example, contact force sensors, pressure sensors, mechanical deformation detection sensors, or ultrasound-based contact sensors. Any type of sensors that are used for ascertaining electrode contact with tissue are referred to herein as 'contact sensors.'

In some embodiments, given that the mechanical contact is sufficient, the system identifies scar tissue by comparing the measured tissue impedance with a baseline impedance. Examples of possible baseline impedances are average tissue impedance and surrounding blood impedance. Techniques to determine baseline impedance are described, for example, in U.S. patent application Ser. No. 15/788,286, filed Oct. 19, 2017, now U.S. Pat. No. 10,398,348, issued on Sep. 3, 2019, entitled "Baseline Impedance Maps for Tissue Proximity Indications," which is assigned to the assignee of the present patent application and whose disclosure is incorporated herein by reference.

A given baseline impedance may be independent of the measure of contact, as long as the contact is sufficient, for example by the measured contact force being larger than a given minimum value. Thus, the measure of contact does not have to be uniform across the heart tissue.

The disclosed technique, which combines electrical impedance measurements with physical contact measurements for ascertaining the quality of the physical contact, and further applies analysis methods using a baseline impedance criterium, may provide reliable identification of intra-cardiac scars. A reliable identification of intra-cardiac scars can assist the physician in diagnosis and in planning a treatment, as well as in the diagnosis and analysis of past treatment outcomes.

System Description

FIG. 1 is a schematic, pictorial illustration of a system 21 for electro-anatomical mapping, in accordance with an embodiment of the present invention.

FIG. 1 depicts a physician 27 using an electro-anatomical catheter 29 to perform an electro-anatomical mapping of a heart 23 of a patient 25. Catheter 29 comprises, at its distal end, one or more arms 20, which may be mechanically flexible, to each of which are coupled one or more electrodes 22. During the mapping procedure, electrodes 22 acquire and/or inject signals from and/or to the tissue of heart 23. A processor 28 receives these signals via an electrical interface 35, and uses information contained in these signals to construct an electro-anatomical map 31. During and/or following the procedure, processor 28 may display electro-anatomical map 31 on a display 26.

During the procedure, the respective locations of electrodes 22 are tracked. Such tracking may be performed, for example, using the aforementioned ACL technique. Per this technique, a plurality of external electrodes 24 are coupled to the body of patient 25; for example, three external electrodes 24 may be coupled to the patient's chest, and another three external electrodes may be coupled to the patient's back. (For ease of illustration, only one external electrode is shown in FIG. 1.) While electrodes 22 are inside heart 23 of the patient, electric currents are passed between electrodes 22 and external electrodes 24. Based on the ratios between the resulting current amplitudes measured at external electrodes 24 (or between the impedances implied by these amplitudes), and given the known positions of electrodes 24 on the patient's body, processor 28 calculates an estimated location of each of electrodes 22 within the patient's heart. The processor may thus associate any given impedance signal received from electrodes 22 with the location at which the signal was acquired.

In an embodiment, processor 28 is further configured to indicate the quality of mechanical contact between each electrode of electrodes 22 and the inner surface of the heart during measurement. The indication is based on modeling flexion of the arms 20 so as to indicate for each electrode, whether the electrode is pressed against tissue (and possibly estimate the extent of contact force).

The example illustration shown in FIG. 1 is chosen purely for the sake of conceptual clarity. Other type of sensing geometries, such as of the Lasso® Catheter (produced by Biosense Webster Inc.) may also be employed. Alternative or additional contact sensors may be fitted at the distal end of electro-anatomical catheter 29. In an embodiment, measurements of some electrodes 22 may be discarded because their contact quality is poor, and the measurements of other electrodes may be regarded valid because their contact quality is high.

In general, processor 28 may be embodied as a single processor, or as a cooperatively networked or clustered set of processors. Processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Intra-Cardiac Scar Tissue Identification

FIG. 2 is a schematic, pictorial illustration of electro-anatomical map 31 of a portion of patient's 25 heart 23, in accordance with an embodiment of the present invention.

As seen, electro-anatomical map 31 indicates two zones by using a gray-scale so as to visualize measured tissue impedance: A zone 50 is indicated as comprising healthy tissue while a zone 52 is classified as scar tissue. Such visualization can be accompanied by a bar 32 for providing further explanation. In bar 32, a line 34 separates scar from healthy tissue, as evident from a legend 36.

In an embodiment, bar 32 represents an impedance scale, where line 34 represents a given baseline impedance. Correspondingly, tissue impedance higher than the given baseline impedance indicates by legend 36 healthy tissue, while tissue impedance equal or lower than the given baseline impedance indicates by legend 36 scar tissue. The given baseline impedance, represented by line 34, may be that of the surrounding blood, or average tissue impedance, for example. Typical blood impedance values are on the order of 90-100 ohms, and during contact with normal tissue the measured impedance may increase by up to 10 percent. The numerical values, however, are given purely by way of example.

The example illustration shown in FIG. 2 is chosen purely for the sake of conceptual clarity. Other visualizations schemes are possible, such a continuous scaling of the measured impedance and/or color coding.

FIG. 3 is a flow chart that schematically illustrates a method of identifying intra-cardiac scar tissue, in accordance with an embodiment of the present invention. The procedure may begin with physician 27 inserting electro-anatomical catheter 29 into the heart, at an insertion step 70.

Next, at a sensing step 72, physician 27 deploys and engages tissue of heart 23 at a given location. System 21 senses impedance through electrodes 22 while at the same time obtaining a measure of their physical contact with tissue.

Processor 28 of system 21 may estimate the quality of mechanical contact of a given electrode 22 with the tissue in any suitable way. In some embodiments, sensors fitted at arms 20 are used, such as contact force sensors, pressure sensors and ultrasound-based contact sensors. In one example embodiment, each arm of arms 20 is fitted with one or more strain sensors that indicate the force with which a flexible arm is pressed against tissue. The measured force indicates the quality of mechanical contact. In another embodiment, the force with which an arm is pressed against tissue is indicated by measuring the flexion of the arm relative to its original shape. Techniques of this sort are described, for example, in U.S. patent application Ser. No. 15/610,865, filed Jun. 1, 2017, entitled "Using a Piecewise-Linear Model of a Catheter Arm to Identify Contact with Tissue," which is assigned to the assignee of the present patent application and whose disclosure is incorporated herein by reference. For example, if a flexible arm 20 is deflected by more than 20 degrees from its unperturbed state, a distal electrode fitted on arm 20 can be considered as in contact. If, for example, the deflection exceeds 35 degrees, proximal electrodes on arm can be also considered as in contact. Generally, however, any suitable type of contact sensor or contact sensing method can be used.

At a location estimation step 74, processor 28 calculates, from one or more electrical current amplitudes measured at external electrodes 24, a respective estimated location of one or more of sensing electrodes 22.

The method now proceeds to a contact verification step 76, in which processor 28 determines based on the calculated measure of contact whether one or more of sensing electrodes 22 are in sufficient contact at the estimated location.

If the determination at decision step 76 is negative, then the method returns to step 72 and physician 27 may reattempt to engage tissue. If the determination at step 76 is affirmative, then the method proceeds to a tissue classification step 78, in which physician 27 (or the processor, automatically) determines whether or not the tissue impedance is lower than a given baseline impedance. If the determination at step 76 is negative, then the processor classifies the tissue at the location in question as healthy, at a healthy tissue indication step 80. If the determination at step 78 is affirmative, then the processor classifies the tissue as scar tissue, at a scar indication step 82.

The method proceeds to a map updating step 84 in which processor 28 marks a part of electro-anatomical map 31 as comprising either healthy or scar tissue. In some embodiments, processor 28 updates part of electro-anatomical map 31 with the measured electrical impedance at the given location, as estimated at in step 74. In an embodiment, processor 28 updates part of electro-anatomical map 31 by incorporating into the map an estimated location of the at least one of the electrodes ascertained to be in contact with tissue at the estimated location.

The procedure may be iterated for multiple locations on the inner surface of heart 23, by moving the catheter so as to engage another location over tissue, at a catheter moving step 86. The method may then return to step 72.

The example flow chart shown in FIG. 3 is chosen purely for the sake of conceptual clarity. In alternative embodiments, various steps may be performed to assess contact quality and to analyze and visualize tissue impedance.

Although the embodiments described herein mainly address pulmonary vein isolation, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for mapping of intra-cardiac scar tissue, the system comprising:
   an electrical interface for communicating with a probe inserted into a heart of a patient; and
   a processor, which is configured to:
   receive, via the electrical interface, (i) a first indication of an electrical impedance measured by the probe at a given location on an inner surface of the heart, and (ii) a second indication of a sufficient level of physical contact between the probe and the inner surface of the heart during measurement of the electrical impedance, wherein receipt of the first and second indications is associated with an estimated location within the heart; and based on the first and second indications, classify tissue at the given location as scar tissue to update an electro-anatomical map.

2. The system according to claim 1, wherein the processor is configured to distinguish, based on the second indication, between the scar tissue and blood.

3. The system according to claim 1, wherein the processor is configured to classify the tissue as the scar tissue by detecting that the tissue has an impedance lower than a given baseline impedance.

4. The system according to claim 3, wherein the baseline impedance comprises a measured blood impedance in the heart.

5. The system according to claim 3, wherein the baseline impedance comprises a measured tissue impedance averaged over a portion of the inner surface of the heart.

6. The system according to claim 1, wherein the processor is configured to receive the second indication from one or more sensors that are fitted at a distal end of the probe.

7. The system according to claim 1, wherein the processor is configured to calculate from the first indication a respective estimated location of the probe in the heart.

8. The system according to claim 7, wherein the processor is configured to update a map of at least part of the heart by incorporating the estimated location of the probe into the map.

9. The system according to claim 8, wherein the processor is configured to update the map with the measured electrical impedance at the estimated location.

10. The system according to claim 8, wherein the processor is configured to differentiate the scar tissue from healthy tissue on the map using at least one of numerical and visual coding.

11. A method for detecting intra-cardiac scar tissue, the method comprising:

receiving, from a probe inserted into a heart of a patient, (i) a first indication of an electrical impedance measured by the probe at a given location on an inner surface of the heart, and (ii) a second indication of a sufficient level of physical contact between the probe and the inner surface of the heart during measurement of the electrical impedance, wherein receipt of the first and second indications is associated with an estimated location within the heart; and based on the first and second indications, classifying tissue at the given location as scar tissue to update an electro-analytical map.

12. The method according to claim 11, wherein classifying the tissue comprises distinguishing, based on the second indication, between the scar tissue and blood.

13. The method according to claim 12, wherein classifying the tissue comprises detecting that the tissue has an impedance lower than a given baseline impedance.

14. The method according to claim 13, wherein the baseline impedance comprises a measured blood impedance in the heart.

15. The method according to claim 13, wherein the baseline impedance comprises a measured tissue impedance averaged over a portion of the inner surface of the heart.

16. The method according to claim 11, wherein receiving the second indication comprises receiving the second indication from one or more sensors that are fitted at a distal end of the probe.

17. The method according to claim 11, and comprising calculating from the first indication a respective estimated location of the probe in the heart.

18. The method according to claim 17, and comprising updating a map of at least part of the heart by incorporating the estimated location of the probe into the map.

19. The method according to claim 18, and comprising updating the map with the measured electrical impedance at the estimated location.

20. The method according to claim 18, and comprising differentiating the scar tissue from healthy tissue on the map using at least one of numerical and visual coding.

* * * * *